United States Patent [19]

Suzuki

[11] 4,029,711

[45] June 14, 1977

[54] 4-HYDROXY-N-BUTYRALDEHYDE FROM ALLYL ALCOHOL AND FORMALDEHYDE

[75] Inventor: Shigeto Suzuki, San Francisco, Calif.

[73] Assignee: Chevron Research Company, San Francisco, Calif.

[22] Filed: Mar. 31, 1976

[21] Appl. No.: 672,362

[52] U.S. Cl. .............................. 260/602; 260/632 R
[51] Int. Cl.² ......................................... C07C 47/02
[58] Field of Search ................................... 260/602

[56] References Cited

UNITED STATES PATENTS

| 2,288,211 | 6/1942 | Schulz | 260/602 |
| 2,967,890 | 1/1961 | Mecorney | 260/611 |
| 3,519,691 | 7/1970 | von Portatius | 260/602 |

*Primary Examiner*—James O. Thomas, Jr.
*Assistant Examiner*—W. B. Lone
*Attorney, Agent, or Firm*—Dix A. Newell; John Stoner, Jr.; W. Keith Turner

[57] ABSTRACT

A process for preparing 4-hydroxy-n-butyraldehyde which comprises contacting allyl alcohol with formaldehyde in the presence of hydrogen fluoride at a temperature in the range from about −100° C to about 10° C.

7 Claims, No Drawings

4-HYDROXY-N-BUTYRALDEHYDE FROM ALLYL ALCOHOL AND FORMALDEHYDE

BACKGROUND OF THE INVENTION

The process of this invention relates to the production of 4-hydroxy-n-butyraldehyde by the hydrogen fluoride-catalyzed reaction of allyl alcohol and formaldehyde.

4-hydroxy-n-butyraldehyde has various uses as an intermediate in the production of organic compounds. For example, 4-hydroxy-n-butyraldehyde is readily hydrogenated to prepare 1,4-butanediol, which is in turn reacted with terephthalic acid to produce a saturated polyester for fiber manufacture. 4-hydroxy-n-butyraldehyde may also be readily cyclized to form 2-hydroxy-tetrahydrofuran.

It is known to produce butyraldehydes from unsaturated alcohols by the "oxo synthesis." The oxo synthesis comprises contacting an olefin with carbon monoxide and hydrogen in the presence of a cobalt salt at elevated temperatures and pressures. A typical example of the use of oxo chemistry to prepare 4-hydroxy-n-butyraldehyde is found in the article of Adkins and Krsek appearing at J. Am. Chem. Soc. 71, 3051–5 (1949). In general, the oxo synthesis proceeds as follows:

$$RCH_2CH=CH_2 + CO + H_2 \rightarrow R-CH_2CH_2CH_2CHO$$

Gamma-hydroxyaldehydes have also been synthesized from tetrahydrofuran by oxidation to prepare the peroxide which can be decomposed or rearranged to the aldehyde. British Pat. No. 614,392 (1948) is typical of this approach, and particularly suggests the use of cobalt or nickel catalysts to promote oxidation to the peroxide.

SUMMARY OF THE INVENTION

It has now been discovered that 4-hydroxy-n-butyraldehyde can be prepared by contacting allyl alcohol with formaldehyde in the presence of hydrogen fluoride at a temperature within the range from about −100° C to about 10° C.

DETAILED DESCRIPTION OF THE INVENTION

The present invention is based upon the finding that allyl alcohol and formaldehyde will react in the presence of hydrogen fluoride to produce 4-hydroxy-n-butyraldehyde.

As is well recognized in the art, allyl alcohol is otherwise known as propenyl alcohol and has the structure

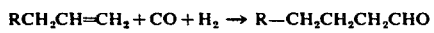

Allyl alcohol is commercially available or may be prepared by hydrolysis of allyl chloride with dilute caustic.

Similarly, formaldehyde is a well-known organic chemical otherwise known as oxymethylene, formic aldehyde or methanol and has the structure

Formaldehyde is commercially available or may be prepared by the catalytic oxidation of low-boiling petroleum gases such as methane or ethane.

In accordance with the process of the present invention, the reaction of allyl alcohol and formaldehyde is carried out in the liquid phase at a temperature within the range from about −100° C to about 10° C, preferably about −70° C to about −10° C, and at a pressure within the range from about 10 psia to about 1000 psia, preferably atmospheric.

Among other factors, the use of a catalyst comprising hydrogen fluoride is believed responsible for the relatively rapid and high conversions obtained under relatively mild reaction conditions. Hydrogen fluoride is also a solvent for the reaction, and is used in excess of catalytic amounts. Satisfactory conversions on the order of about 95% have been obtained in as little as 50 minutes using an HF:reactant weight ratio of from about 1:1 to about 10:1, preferably from about 2:1 to about 5:1. Hydrogen fluoride, per se, is of course a suitable catalyst for use in the present process. However, in actual practice, non-interfering amounts of various diluents and contaminants may be present in the catalyst composition. Thus, suitable hydrogen fluoride catalysts comprise hydrogen fluoride, but may also comprise inert components such as water and dichloromethane. In addition to superior activity as a catalyst in the present process, hydrogen fluoride is relatively easy to separate from the reaction zone effluent. Since the boiling point of HF is 19.7° C at one atmosphere pressure, which is considerably more volatile than 4-hydroxy-n-butyraldehyde, the HF is readily separated by distillation and recycled to the reaction zone. Some unreacted formaldehyde may also be codistilled with HF and be recycled to the reaction zone.

The molar ratio of formaldehyde to allyl alcohol which provides acceptable yields will vary depending upon precise reaction conditions. However, for general guidance, acceptable molar ratios of formaldehyde to allyl alcohol will range from about 1:1 to about 10:1, preferably from about 2:1 to about 4:1. Within these ranges it has been found that as the molar ratio of formaldehyde to allyl alcohol decreases below 2:1, increasing quantities of 4-allyloxy-n-butyraldehyde are found in the crude product.

The crude reaction product comprising 4-hydroxy-n-butyraldehyde may be purified in any of several ways. For example, hydrogen fluoride, and the unreacted formaldehyde and allyl alcohol may be removed by distillation under reduced pressure to leave 4-hydroxy-n-butyraldehyde as a bottoms product; or hydrogen fluoride and formaldehyde may be removed by distillation, and the butyraldehyde separated from allyl alcohol as a bisulfite addition compound, which is readily decomposed into the original aldehyde by contact with aqueous acid. Also where the 4-hydroxy-n-butyraldehyde is intended as a feedstock in 1,4-butanediol production, the entire bottoms product after HF removal may be hydrogenated. The resulting diol may then be recovered by conventional distillation techniques.

EXAMPLES

The following examples illustrate the process of the invention. Those familiar with the art will recognize that modifications and variations of the illustrative examples may be made in the practice of the invention.

EXAMPLE 1

Preparation of 4-hydroxy-n-butyraldehyde

A 100-ml stainless-steel autoclave was charged with 8.7 grams (0.15 mols) of allyl alcohol, 9.0 grams (0.3 mols) of formaldehyde and 76 grams (3.8 mols) of hydrogen fluoride. The autoclave was maintained at about −45° C for 50 minutes. Hydrogen fluoride was distilled from the reaction product and the distillation bottoms were analyzed by vapor phase chromatography using isobutyl alcohol as a standard.

Conversion of formaldehyde was essentially complete, i.e., over 95% and a 40.5% yield of 4-hydroxy-n-butyraldehyde was obtained.

EXAMPLES 2-12

In accordance with the general procedure of Example 1, 4-hydroxy-n-butyraldehyde was prepared under a variety of reaction conditions. The results are summarized in Table I.

TABLE I

| | | REACTION CONDITIONS | | | | | | | PRODUCT | | | |
|---|---|---|---|---|---|---|---|---|---|---|---|---|
| Ex. No. | Allyl Alcohol Mols | Form-aldehyde Mols | HF Mols | H₂O Mols | Other Name | Other Mols | Temp. °C | Time Min. | Conversion % | 4-hydroxy-n-butyral-dehyde % | 4-allyloxy-n-butyral-dehyde % | Other |
| 2 | 0.1 | 0.1 | 1.25 | 0 | H₂SO₄ | 0.26 | −45 | 60 | no reaction | | | |
| 3 | 0.13 | 0.13 | 2.5 | 0 | none | — | −70 | 30 | 93 | 18 | 53 | — |
| 4 | 0.07 | 0.28 | 2.5 | 0 | None | — | −45 | 30 | 90 | — | — | — |
| | | | | | | | | 60 | >95 | 32.4 (1) | — | — |
| 5 | 0.07 | 0.07 | 2.5 | 0.35 | None | — | −30 | 30 | high | — (2) | — (2) | — |
| 6 | 0.07 | 0.1 | 2.5 | 0.2 | None | — | −45 | 30 | 95 | — | — | — |
| | | | | | | | | 60 | >95 | 22 | 10 | — |
| 7 | 0.1 | 0.2 | 2.75 | 0.15 | None | — | −45 | 60 | — | — (3) | — (3) | — |
| | | | | | | | | 90 | — | 15 (3) | — (3) | — |
| 8 | 0.07 | 0.07 | 2.5 | 0 | HOAC | 0.21 | −30 | 30 | — | 6 | 14 | — |
| 9 | 0.07 | 0.17 | 2.5 | 0 | None | — | −30 | 20 | >95 | — (4) | — | — |
| 10 | 0.07 | 0.17 | 2.5 | 0 | None | — | −45 | 30 | >95 | 34 | 18 | 1.2 (5) |
| 11 | 0.1 | 0.2 | 2.5 | 0 | CH₂Cl₂ | 0.63 | −45 | 60 | >95 | 32 (6) | 18 (6) | — |
| 12 | 0.1 | 0.2 | 2.75 | 0.15 | CH₂Cl₂ | 0.63 | −45 | 60 | — | — | — | — |

Footnotes
(1) Catalytic hydrogenation of the crude reaction product gave a 34% yield of 1,4-butanediol.
(2) Catalytic hydrogenation of the crude reaction product gave an 11% yield of 1,4-butanediol and 16% yield of 4-propyloxybutanol.
(3) After 60 minutes the ratio of 4-hydroxy-n-butyraldehyde:4-allyloxy-n-butyraldehyde was 0.3; after 90 minutes the ratio was 3.0.
(4) Catalytic hydrogenation of the crude reaction product gave a 12% yield of 1,4-butanediol.
(5) 2,3-dihydrofuran.
(6) After 60 minutes the ratio of 4-hydroxy-n-butyraldehyde:4-allyloxy-n-butyraldehyde was 0.4; after 90 minutes the ratio was 2.7.

Example 2 shows that a strong protonic acid, such as sulfuric acid, completely inhibits the reaction, and thereby illustrates the uniqueness of hydrogen fluoride in this reaction. Example 3 produced more of the intermediate compound, 4-allyloxy-n-butyraldehyde, indicating a slower reaction at −70° C. Example 4 illustrates that catalytic hydrogenation gives a quantitative yield of 1,4-butanediol from the 4-hydroxy-n-butyraldehyde. Examples 5, 6, and 7 illustrates that water can be added to the reaction system. Example 7 also shows the rapid production of 4-allyloxy-n-butyraldehyde which is then converted to 4-hydroxy-n-butyraldehyde as the reaction proceeds. Example 8 indicates that a weak organic acid such as acetic acid may be present in the reaction medium. As in Example 7, Example 9 shows that there is a rapid conversion of allyl alcohol, but that the yield of products is still low after only 20 minutes. Example 10 illustrates use of the preferred formaldehyde: allyl alcohol ratio of 2:1. Examples 11 and 12 show that an inert substance, such as dichloromethane may be present in the reaction medium.

While the process of this invention has been illustrated by the above examples, various modifications will be apparent to those skilled in the art. Accordingly, the examples are not intended to limit the scope of the invention as defined by the following claims.

What is claimed is:

1. A process for preparing 4-hydroxy-n-butyraldehyde which comprises contacting allyl alcohol and formaldehyde in the presence of hydrogen fluoride at a temperature from about −100° C to about 10° C and a pressure of from about 10 psia to about 1000 psia.

2. A process according to claim 1 wherein the hydrogen fluoride to reactant weight ratio is from about 1:1 to about 10:1.

3. A process according to claim 2 wherein the hydrogen fluoride to reactant weight ratio is about 5:1.

4. A process according to claim 1 wherein the molar ratio of formaldehyde to allyl alcohol is from about 1:1 to about 10:1.

5. A process according to claim 4 wherein the molar ratio of formaldehyde to allyl alcohol is from about 2:1 to about 4:1.

6. A process according to claim 1 wherein the temperature is from about −70° C to about −10° C and the pressure is atmospheric.

7. A process according to claim 1 wherein the molar ratio of formaldehyde to allyl alcohol is about 2:1, the hydrogen fluoride to reactant weight ratio is about 5:1, the temperature is from about −70° C to about −10° C, and the pressure is atmospheric.

* * * * *